United States Patent [19]

Rosenthal

[11] Patent Number: 4,487,278
[45] Date of Patent: Dec. 11, 1984

[54] INSTRUMENT FOR PROVIDING AUTOMATIC MEASUREMENT OF TEST WEIGHT

[75] Inventor: Robert D. Rosenthal, Gaithersburg, Md.

[73] Assignee: Trebor Industries, Inc., Gaithersburg, Md.

[21] Appl. No.: 525,884

[22] Filed: Aug. 24, 1983

[51] Int. Cl.³ .................. G01G 19/52; G01N 9/02
[52] U.S. Cl. ................................ 177/25; 177/1; 177/50; 177/DIG. 6; 364/498; 73/32 R; 73/433
[58] Field of Search ............. 177/25, 50, DIG. 6; 364/498, 554, 562–564, 567; 73/32 R, 433; 366/336, 337

[56] References Cited

U.S. PATENT DOCUMENTS 4,286,327 8/1981 Rosenthal et al. .
4,404,642 9/1983 Rosenthal .................. 364/498 X

FOREIGN PATENT DOCUMENTS 401892 2/1974 U.S.S.R. ........................ 177/50

OTHER PUBLICATIONS

Circular No. 921, U.S. Department of Agriculture, Jun. 1953, Washington, D. C.

Primary Examiner—E. A. Goldberg
Assistant Examiner—F. L. Kampe
Attorney, Agent, or Firm—Bernard, Rothwell & Brown

[57] ABSTRACT

An instrument for automatically and accurately determining the "test weight" of grain, utilizes a confined column having a constant cross sectional area with means for sequentially dumping a plurality of batches of grain from the column and weighing the batches as dumped, combined with means for detecting the height of the grain in the column before or after each dump and feeding the information as to the height and weight to a microprocessor to determine the weight per unit volume utilizing linear regression equations. The instrument also includes an infrared spectroscopic detection device for determining moisture, protein, and oil content.

11 Claims, 3 Drawing Figures

INSTRUMENT FOR PROVIDING AUTOMATIC MEASUREMENT OF TEST WEIGHT

BACKGROUND OF THE INVENTION

1. Field of the Invention

This invention relates to improvements in determining the test weight of grain, and more particularly for doing it automatically, accurately and inexpensively.

2. Prior Art

The test weight per bushel of grain (usually shortened and referred to as "test weight") is an important factor in assigning a grade to a lot of grain under the official grain standards of the United States. It is therefore essential that the test weight per bushel be accurately determined as it affects the market value of the grain.

An apparatus for determining test weight per bushel for grain was designed by the U.S. Department of Agriculture for determining test weight per bushel of various grains. This standard weight-per-bushel tester is described in Circular 921 June 1953 USDA which superseded USDA Bulletin 1065 issued May 1922. The apparatus includes a stand, a filling hopper, a test kettle, a weighing beam, an overflow pan and a stroker. The user pours about one and one-fourth quarts of grain into the filling hopper that has a stopper in its base. The bottom of the hopper is two inches above a one-quart cylindrical test kettle. The stopper is released and the grain flows through the hopper overflowing the test kettle. The operator then uses the standard stroker to level the grain along the top of the test kettle and then he weighs the container on a beam scale. The use of this USDA designed standard test weight apparatus is clumsy, slow and inefficient in the use of personnel even though it is accurate and it is the legal standard. There has been a long-standing need in the art to provide test weight per bushel automatically, inexpensively and with as much accuracy as the USDA standards apparatus, but without the deficiencies as outlined above.

In measuring "test weight" (generally defined as volume of grain divided by its weight) three different types of errors are encountered, namely, errors in measuring volume, errors due to compaction, and errors in measuring weight. As to errors in measuring volume, if it is assumed that a cross-sectional area is known in constant then this error is only a function of the accuracy in measuring height. In the USDA legally accepted procedure, described above, this error in height is negligible for two reasons: (1) a large cup is used, thus a small error in height is negligible in calculating cup volume and, (2) by pushing a leveling stick across the top surface of the cup, error in height is minimal. Errors due to compaction occur since grain kernels vary significantly in size and shape and the amount that can fit into a fixed volume can also vary considerably. In the USDA test weight procedure this compaction error is minimized by loading the cup from a fixed geometry funnel located a fixed distance above the cup. Errors in weighing accuracy obviously would cause an error in the test weight. In the USDA test weight procedure a large weight of sample is used, e.g., about 700 to 1,000 grams. Since the accuracy of most high quality scales is independent of the weight placed on the scale and scale accuracy in the grain industry is normally about 0.1 gram, any error of 0.1 gram is negligible when compared to the 700 to 1,000 grams of grain.

Errors in measuring height accurately are magnified if one uses a small diameter container. For example, assuming a two-inch circular cylinder with a height of grain of about four inches determined by optical techniques with a possible error of 0.1 inch and assume that the grain weighs 40 grams, the possible error will calculate to a 2.5% error which is more than 10 times that allowable under the official USDA procedure. It is believed that this is the principal reason that optical height measurement has not previously been used for test weight determination. Note, that for larger grains such as corn the possible error might be three to five times larger than the above example.

Errors due to the need for consistent compaction are not related to the accuracy of the height measurement. An instrument known in the art made by Dickey-John Corp. includes a small sample cup, about two inches in diameter and four inches deep. This cup after being filled is leveled off with a solenoid-actuated leveling device, and by weighing the empty and full cup, test weight is calculated. The Dickey-John system, however, does not provide the required accuracy, and the reason is thought to be based on how the cup is filled with grain, i.e., the grain is compacted into the cup in varying amounts and this variation in compacted weight is perhaps ten times higher than the allowable tolerance by the USDA.

Also known in the art and commonly available on the market for use in the agricultural sector of the economy are near infrared instruments for measuring protein, moisture and oil in grain products. Such instruments, such as the Trebor 90 made by Trebor Industries, Inc. in Gaithersburg, MD, allows an unskilled user to determine the protein, moisture and oil constituents of a grain sample in a few seconds. In performing such measurement a quantity of grain is poured into the Trebor 90 hopper and near infrared energy is passed through the sample while it is in a column below the hopper. The operation is further disclosed in U.S. Pat. No. 4,286,327. There is a need in the field to allow the same unskilled user who determines the protein, moisture and oil constituents utilizing the Trebor 90 to also automatically determine the test weight per bushel of the same grain whose chemical constituents are being tested. It would also be highly desirable to eliminate the requirement for a separate test and test instrument to determine the test weight per bushel of grain.

SUMMARY OF THE INVENTION

This invention provides an instrument for automatically and accurately determining the test weight of grain utilizing a confined column of constant cross-sectional area for containing the grain to be tested for test weight per bushel volume. Grain is fed to the column via baffles to help dissipate its kinetic energy and fills the column to a height which is electro/optically measured. At the bottom of the test column grain is removed in discrete batches and each removed batch is weighed. This causes the remaining grain in the column to have relatively constant packing density. At the time the batches are removed the column will fall and the height of the column is automatically determined to give an indication of volume. The weight and height (volume) of each batch are fed into a microprocessor and the test weight per bushel is determined utilizing linear regression equations.

By the use of this invention a highly accurate measuring and testing instrument is provided which can be incorporated in the same instrument for measuring protein, oil and moisture and operated simultaneously. Errors in height and weight are minimized by using linear regression analysis in multiple measurements. Errors in inconsistent packing are minimized because of the grain feed mechanism and the rotational effect of the grain removal via pockets in a discharge wheel.

DETAILED DESCRIPTION OF PREFERRED EMBODIMENT

Figure 1:
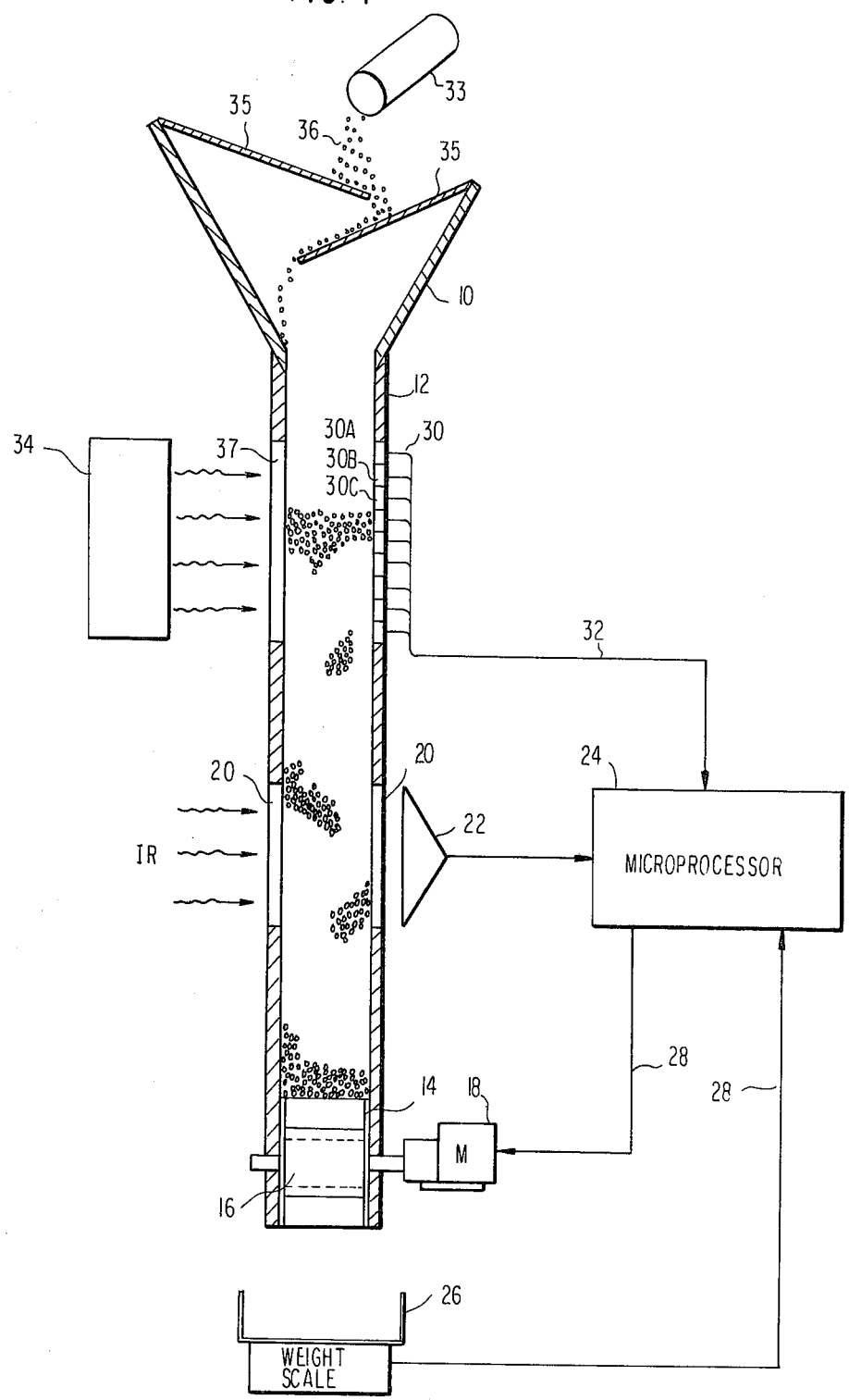
FIG. 1 is a schematic view of the instrument of this invention.

With reference to FIG. 1 a funnel shaped hopper 10 which can conveniently be the hopper of a Trebor 90 grain instrument leads into a column 12 having a constant cross-sectional area so that the height of grain in the column is readily translated into volumne. The column may contain a sample of grain to be tested therein. Near the bottom of the column a dump wheel 14 is provided having a plurality of dumping pockets 16. Dump wheel 14 is driven by an electric motor 18.

In the use of the present invention in a Trebor 90 or similar infrared detection instrument there would be infrared transparent windows 20 with infrared radiation directed through the grain sample from one side of the column through the windows to a detector 22 which then feeds the information to a microprocessor 24 as described in more detail in U.S. Pat. No. 4,286,327.

At the bottom of the column directly below the dump wheel 14 there is a weighing scale 26 producing an electrical output signal proportional to weight, which signal is transmitted on line 28 to the microprocessor 24.

After each batch is dumped by dump pockets 16 of the dump wheel 14, the height of the grain remaining in the column 12 is determined by means including a segmental silicon array 30 having a plurality of linear vertically-arranged segments 30A, 30B, 30C, etc. which produce outputs on line 32 to the microprocessor 24. A suitable source of radiation 34 is directed through the transparent window 37 opposite the segmented silicon array 30. Although such a sequential silicon array is perfectly usable, another approach is also usable. This other approach uses a single axis position-sensing photodiode where the shadow of the grain gives an output signal proportional to the height. A detector similar to United Detector Technology, Inc.'s PIN-LSC/4 position-sensing detector could be used.

The pocketed dump wheel 14 assists in causing the grain to have a reasonably consistent density. This is accomplished because the dump wheel provides an "impact" type load as the wheel fills up its pockets and rotates. This impact load assists the kernels in reaching a constant density. In addition, grain 36 which is dumped into the instrument from a cup 33 is deflected by baffles 35. These baffles cause the free-falling grain to bounce and thereby dissipate some of the grain's kinetic energy to cause a more consistent grain entry into the measuring chamber 12. The baffles 35 also serve a second function to protect the optical measuring apparatus from external light as such external light might interfere with the optical measurements.

In use an operator dumps a sample of grain to be tested to determine the test weight per bushel, and also if desired to determine moisture, protein or oil content, into hopper 10. The grain sample fills up column 12 to cover at least a part of a segmented silicon array 30. The IR detector 22 can make its determination of the moisture protein or oil, e.g. as taught in U.S. Pat. No. 4,286,327. At the same time the test weight per bushel can be determined by this invention. This is accomplished by motor 18 driving pocketed wheel 14 to dump sequential batches of the grain onto the weight scale 26. Before and after each batch is dumped the height of the grain in the column is determined. The difference in height will directly relate to the volume of the grain per unit of weight as measured by the weight scale 26. Signals corresponding to these values are fed via the lines 28 and 32 into the microprocessor 24 wherein they are applied to a linear regression equation to determine the test weight, see FIG. 2.

Figure 2:
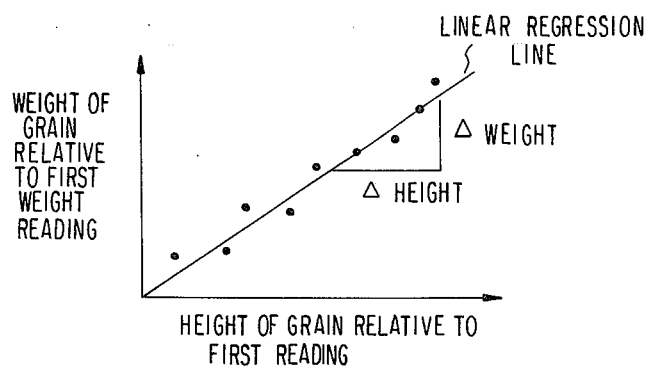
FIG. 2 is a graph plotting measurement of weight and column height (volume) and shows a linear regression equation line plotted thereon.

With regard to FIG. 2 the test weight equals $C \times K$ where K is the slope of the linear regression line (i.e., $\Delta$ weight/$\Delta$ height) and C equals a conversion constant. The value of C varies for different types of grain, i.e., C for wheat will differ from C for corn, etc.

In initial start up and before test operation, the first two dumps of the ejector wheel, i.e., the first two times the motor is turned on, are not used for determining height or weight. The reason for this is that the first two dumps cause the grain to have relatively constant compaction in the column.

Figure 3:
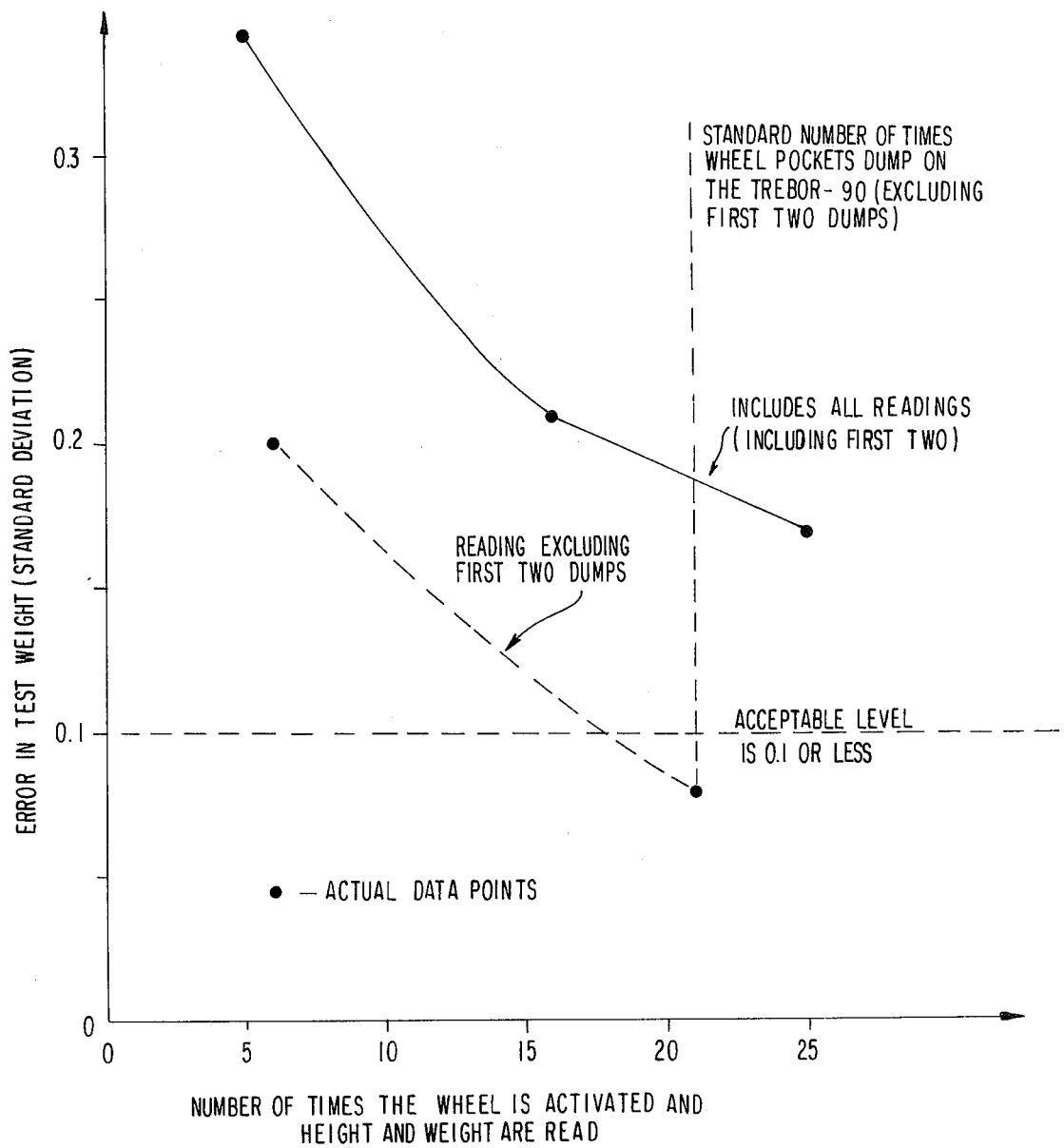
FIG. 3 is a plot of error in test weight using this invention versus the number of times the discharge wheel is activated, and the height and weight read.

FIG. 3 is a plot of error in the test weight against the number of times the wheel pockets dump and height and weight is read. On the Trebor 90 the motor is turned on 23 times for a short time, approximately 1 second. By excluding the first two dumps the error is less than 0.1% as actually measured. Thus the percentage error is significantly decreased by excluding the first two dumps.

In carrying out the invention, and as a nonlimiting example the column 12 and hopper 10 are part of a Trebor 90 grain tester as is the dump wheel 14 which has three pockets and is driven by a D.C. geared motor 18 (Barber-Coleman Model No. CY QM 62810-29). The weight scale 26 is manufactured by Sartorius Scale, Model No. 1003. A position detector Model No. PIN-LSC/4 by United Detector Technology is used instead of a silicon array. The microprocessor 24 is an Intel 8085A as incorporated in Trebor's single board Model No. ICB-85.

The invention produces results which are compared with the USDA standard test and the differences are negligible, i.e., within 0.1% (standard deviation). Use of the invention saves considerable time and labor while producing extremely accurate results. Also while the invention is useful in combination with an infrared detection instrument it is not necessary that it be combined with such instrument.

I claim:

1. An instrument for automatically and accurately determining the test weight per bushel of grain, comprising:
   (a) a confined column having a constant cross sectional area for containing grain to be tested for weight per bushel,
   (b) means for sequentially dumping a plurality of batches of grain to be tested from the bottom of the column, (c) means for automatically determining the height of the grain in the column prior to and after the dumping of each batch of grain from the column, (d) weighing means for weighing each batch of grain dumped from the column, (e) microprocessor means receiving information from the weighing means and the height of the grain column detecting means and calculating the weight per bushel.

2. An instrument for automatically determining the test weight per bushel for grain as in claim 1 wherein the column is a portion of a near infrared detection instrument for determining moisture, protein, oil or like constituents of the same grain.

3. An instrument for automatically determining the test weight per bushel for grain as in claim 1 or 2 wherein the automatic height determining means is an optical detection means providing output signals proportional to height of grain in the column.

4. An instrument for automatically determining the test weight per bushel for grain as in claim 1, 2 or 3 wherein the means for weighing is a scale with an electrical output signal proportional to weight which is fed to the microprocessor.

5. An instrument for automatically determining the test weight per bushel for grain as in claim 1, 2, 3, or 4 wherein the means for dumping is a rotatable dump wheel with dump pockets on its periphery, positioned at the bottom of the column and driven by a motor.

6. An instrument for automatically determining the test weight per bushel of grain as defined in claim 1 further comprising baffles at the top of the column to deflect the kinetic energy of grain fed to the column.

7. An instrument for automatically determining the test weight per bushel of grain as defined in claim 1 wherein the microprocessor utilizes linear regression equations.

8. An instrument for automatically determining the test weight per bushel of grain as defined in claim 1 wherein the microprocessor excludes the first two batches of grain weighed.

9. An instrument for automatically and accurately determining the weight per unit volume of grain, the instrument comprising:

(a) a confined column having a constant cross-sectional area for containing grain to be tested for weight per bushel, (b) means for sequentially dumping a plurality of batches of grain to be tested from the bottom of the column, (c) means for automatically determining the height of the grain in the column prior to and after the dumping of each batch of grain from the bottom column, (d) weighing means for weighing each batch of grain dumped from the column, (e) data processing means connected to receive signals from the weighing means and signals from the height of the grain column detecting means, the data processing means calculating the weight per unit volume utilizing linear regression equations after the first two batches are dumped.

10. An instrument for automatically determining the test weight per bushel for grain as in claim 8 wherein the column is a portion of a near infrared detection instrument for determining moisture, protein, oil or like constituents of the same grain.

11. A method of automatically determining the weight per unit volume of grain comprising;

(a) pouring grain into a columnar zone of a constant cross-sectional area so that the height of grain in the column is readily translatable to volume, (b) dumping small batches of grain from the bottom of the columnar zone so that each batch dumped decreases the height of the grain in the columnar zone, (c) weighing accurately the weight of each batch dumped, (d) measuring accurately the height of the grain in the columnar zone after each batch is dumped, (e) automatically calculating the test weight per unit volume using the change in weight and change in height measurements as applied to linear regression equations after excluding the first several batches.

* * * * *

UNITED STATES PATENT AND TRADEMARK OFFICE
CERTIFICATE OF CORRECTION

PATENT NO. : 4,487,278
DATED : December 11, 1984
INVENTOR(S) : Robert D. Rosenthal It is certified that error appears in the above-identified patent and that said Letters Patent is hereby corrected as shown below:

Column 6, Claim 10, line 2, delete "claim 8" and substitute therefor -- claim 9 --.

Signed and Sealed this

Sixteenth Day of July 1985

[SEAL]

Attest:

DONALD J. QUIGG

Attesting Officer

Acting Commissioner of Patents and Trademarks